United States Patent [19]
Barnett

[11] Patent Number: 6,078,178
[45] Date of Patent: Jun. 20, 2000

[54] WATER QUALITY INDICATING APPARATUS HAVING SELF-CLEANING TEST PROBES

[75] Inventor: Charles N. Barnett, Roselle, Ill.

[73] Assignee: U.S. Filter Corporation, Palm Desert, Calif.

[21] Appl. No.: 09/198,231

[22] Filed: Nov. 23, 1998

[51] Int. Cl.[7] .................................................. G01N 27/02
[52] U.S. Cl. .......................... 324/439; 324/71.1; 270/85
[58] Field of Search .................... 324/439, 71.1, 324/442, 446, 444; 327/68, 70, 77, 89; 270/85, 746, 96.1, 96.2

[56] References Cited

U.S. PATENT DOCUMENTS

| | | |
|---|---|---|
| 4,257,887 | 3/1981 | Rak et al. . |
| 4,299,698 | 11/1981 | Rak et al. . |
| 4,496,906 | 1/1985 | Clack . |
| 4,623,451 | 11/1986 | Oliver . |
| 4,885,081 | 12/1989 | Oliver . |
| 5,699,272 | 12/1997 | Zabinski . |

FOREIGN PATENT DOCUMENTS

| | | |
|---|---|---|
| 2128176 | 4/1984 | United Kingdom . |
| 2128176A | 4/1984 | United Kingdom . |

*Primary Examiner*—Josie Ballato
*Assistant Examiner*—Vincent Q. Nguyen
*Attorney, Agent, or Firm*—Greer, Burns & Crain, Ltd.

[57] ABSTRACT

Water purity indicating apparatus is adapted to operate on AC input power and includes a housing and a pair of test probes extending from the housing for measuring a resistance of water. Also included is a circuit connected to the test probes and provided within the housing for outputting a signal indicating a purity level of the water based on a first AC voltage generated as a result of the measured resistance of the water.

18 Claims, 2 Drawing Sheets

WATER QUALITY INDICATING APPARATUS HAVING SELF-CLEANING TEST PROBES

BACKGROUND OF THE INVENTION

This invention generally relates to water quality or purity indicators, and specifically to a water quality indicator which is adapted to operate on AC input power to prevent contaminant build-up on the indicator test probes.

Many of the conventional water purifying systems in use in homes or in industries are equipped with a water purity indicator which measures the purity level or level of contaminants in the water. The purity indicators provide useful information as to whether the water is fit for its intended purposes. Typically, the known purity indicators include a pair of test probes or electrodes which are connected to a circuitry, which detects contaminants in the water by measuring the electrical conductivity or resistivity of the water. This is a reliable method for determining the purity of water, since the conductivity of water is directly proportional to the quantity of ionizable dissolved solids, such as minerals, normally found in impure water. The purity level of the water is obtained by comparing the measured conductivity value with a predetermined reference conductivity value. For example, if the measured conductivity falls below the reference value, the condition of the water would be considered acceptable for its intended purposes. On the other hand, if the measured conductivity exceeds the reference value, then it would suggest that the water is contaminated to the point that it would not be acceptable for its intended purposes. Displays such as light emitting diodes (LED) are typically employed to indicate the condition of water to a user.

A common feature of the conventional water purity indicators is that they are operated by DC input power, including the current that is applied to the test probes for measuring the conductivity or resistivity of water. As a consequence, salts or dissolved minerals in the water accumulate on the probes due to electrolytic reaction, thereby degrading the accuracy of the conductivity readings.

One known method for preventing contaminant build-up on the probes is disclosed in U.S. Pat. No. 4,885,081, which is a continuation of U.S. Pat. No. 4,623,451. These patents teach solving this problem by applying a pulsating DC current to the probes or electrodes to "cancel out" the electrolytic reaction. A disadvantage of this method, however, is that an additional circuitry would have to be implemented for performing the "cancel out" process, thereby increasing the cost and the complexity of the overall circuitry of the purity indicator.

Thus, it is a first object of the present invention to provide an improved water purity indicator which prevents contaminants from coating the test probes of the purity indicator without employing additional circuitry dedicated specifically for this purpose.

It is another object of the present invention to provide an improved water purity indicator which applies an AC voltage directly to the test probes of the indicator.

Still another object of the present invention is to provide an improved water purity indicator which compares the AC voltage generated by the resistivity of water with an AC reference voltage in determining the purity of the water.

BRIEF SUMMARY OF THE INVENTION

The above-identified objects are met or exceeded by the present water purity indicator which obtains the purity level of water by measuring the conductivity or resistivity of the water. The advantage of the invention is that an AC voltage is applied directly to the test probes which measure the water conductivity. In this manner, contaminants in the water are prevented from adhering to the test probes and causing inaccurate readings. Thus, accurate conductivity readings can be obtained with a relatively decreased number of circuit components.

More specifically, the present invention is directed to a water purity indicating apparatus which is adapted to operate on AC input power, and includes a housing and a pair of test probes extending from the housing for measuring a resistance of water. Also included is circuitry connected to the test probes and provided within the housing for outputting a signal indicating a purity level of the water based on an AC voltage generated as a result of the measured resistance of the water.

The invention also relates to an AC power operated apparatus for measuring a resistance of water, and includes at least one reference resistor for providing a reference resistance. A pair of test probes operatively connectable to the reference resistor measures the resistance of the water. A reference voltage generating circuit is also included for generating an AC reference voltage. A comparator is provided for comparing the reference voltage with a second AC voltage produced by the reference resistance and the water resistance, and generating a signal indicating the resistance of water relative to the reference resistance.

DETAILED DESCRIPTION OF THE INVENTION

Figure 1:
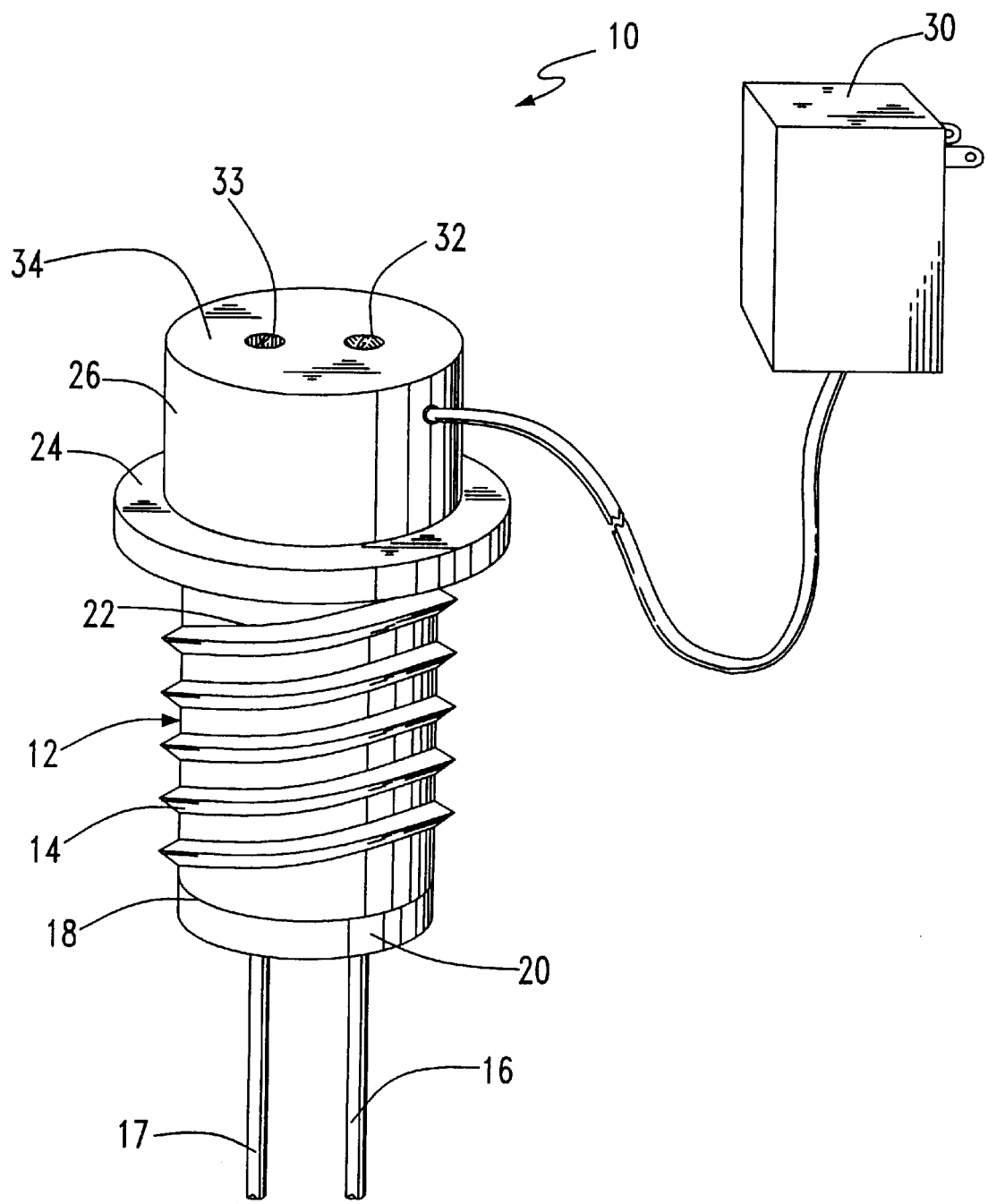
FIG. 1 is a perspective view of a water purity indicator embodying the present invention.

Referring to FIG. 1, a water quality or purity indicator is shown and generally designated 10. The indicator 10 includes a generally cylindrical housing 12 made of an electrically nonconductive material and having a threaded shank portion 14. A pair of spaced probes or electrodes 16, 17 originate from within and extends from a bottom 18 of the housing 12. A grommet 20 holds the probes 16, 17 apart and provides a water tight seal around the bottom 18 of the housing 12. Provided at a top 22 of the housing 12 is a collar 24 which has a greater diameter than that of the housing, and on the top of the collar 24 is a circuit box 26 which encases the circuitry 28 (shown in FIG. 2) of the invention. The circuitry 28 receives its input power from an AC power transformer unit 30. In the preferred embodiment, a pair of light emitting diodes (LED) 32, 33 are also encased in the circuit box 26 and connected to the circuitry 28. When illuminated, the LED's 32, 33 are visible through the top 34 of the circuit box 26, which is transparent.

In operation, the purity indicator 10 is mounted onto a container (not shown) which holds the water to be tested by engaging the threaded shank portions 14 of the housing 12 with complementary threads in a receiving receptacle (not shown) of the container. In this manner, the probes 16, 17, which are electrically connected to the circuitry 28, are made to be immersed in the water. When AC power is applied to the circuitry 28, the conductivity of the water is measured between the probes 16, 17 and one of the two LED's 32, 33 is activated to indicate whether or not the purity level of the water is acceptable with respect to a reference purity level. For example, the LED's 32, 33 might be green and red, indicating acceptable (green) and unacceptable (red) purity levels, respectively.

Figure 2:
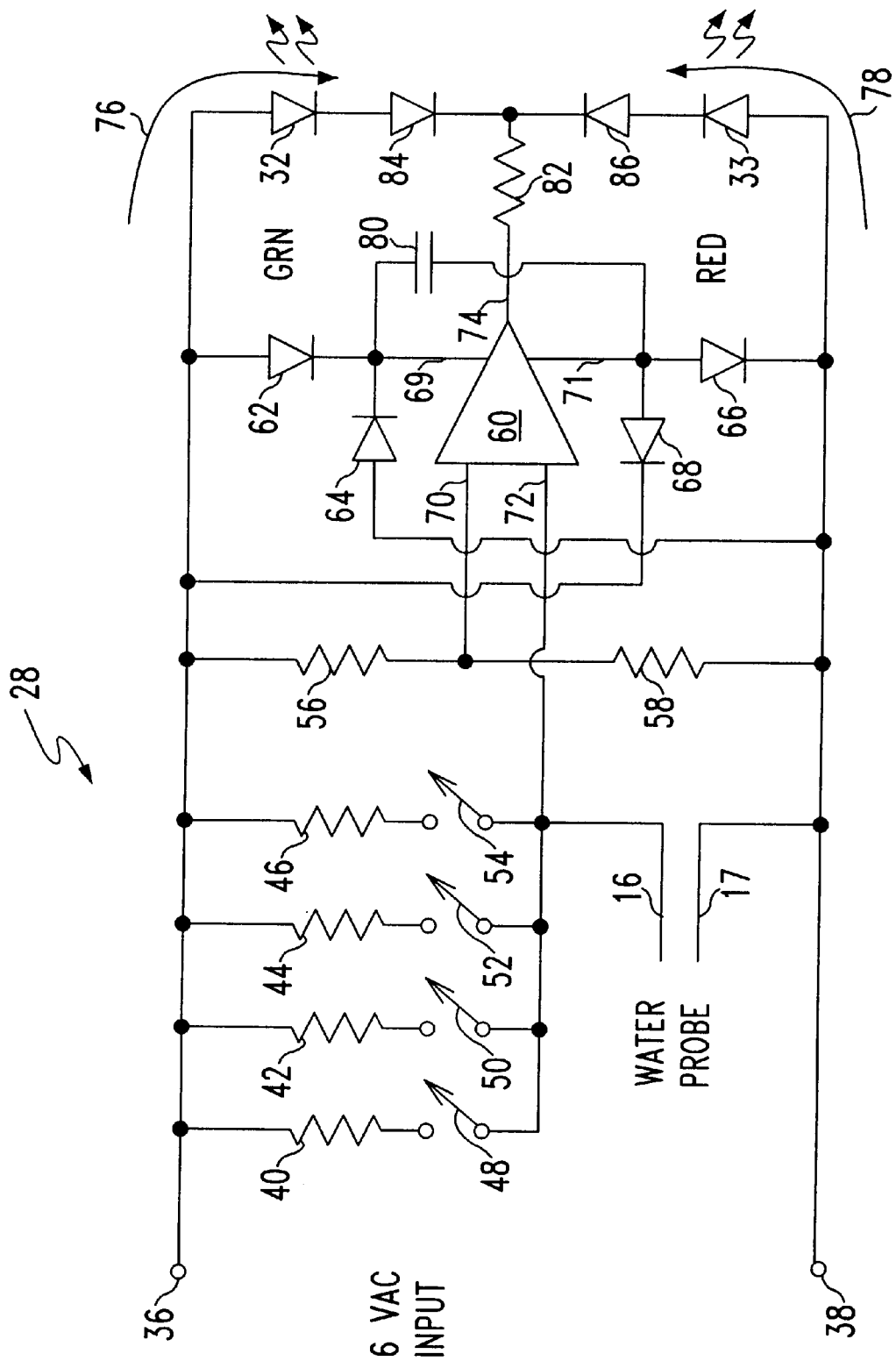
FIG. 2 is a detailed electrical schematic diagram of the circuitry of the water purity indicator of FIG. 1.

Referring now to FIG. 2, the circuitry 28 of the purity indicator 10 includes power input terminals 36, 38 which are connected to the power transformer unit 30 (best seen in FIG. 1). The power transformer 30 is adapted to transform a much higher AC voltage, for example, 120 VAC or 220 VAC, into a preferred 6 VAC and supplies this voltage to the input terminals 36, 38. In the preferred embodiment, each of four parallel reference resistors 40, 42, 44, 46 is connected at one end to the input terminal 36 and the other end to four corresponding parallel reference switches 48, 50, 52, 54, which in turn are connected to the electrode 16. The other probe 17 is connected to the terminal 38. It will be appreciated that the number of reference resistors may vary depending on the application. In some cases, a single reference resistor may be selected by the designer or customer, and others broken off during assembly, when the ultimate work environment or the unit 10 is known.

Also included in the circuitry 28 are two fixed resistors 56, 58 connected in series between the power input terminals 36, 38. Additionally, a comparator 60 is also connected between the input terminals 36, 38 via four diodes 62, 64, 66, 68. In the preferred embodiment, the comparator 60 is a conventional operational amplifier configured to operate as a comparator. One of ordinary skill in the art will recognize that the four diodes 62, 64, 66, 68 are arranged to form a full-wave AC to DC rectifier for providing DC operational current to the comparator 60 across terminals 69 and 71.

The comparator 60 has two input terminals 70, 72. The input terminal 70 receives an AC voltage taken between the two resistors 56, 58 as its input, and the input terminal 72 receives an AC voltage taken between the probe 16 and the reference switches 48, 50, 52, 54, as its input. In the preferred embodiment, the two resistors 56, 58 have the same resistance, and accordingly, the voltage applied to the terminal 70 will be proportional to the input voltage supplied to the input terminals 36, 38 by the power transformer unit 30 (best seen in FIG. 1). On the other hand, the voltage supplied to the input terminal 72 will vary according to the reference resistor 40, 42, 44, 46 selected and the resistance of the water. Connected in this manner, the comparator 60 activates the green LED 32 via an output terminal 74 when the purity level of the water is acceptable, and the red LED 33 when the purity level not acceptable.

In the preferred embodiment, the circuitry 28 is realized utilizing the following components:

GRN LED 32 T1¾ Translucent, 8mA LED
RED LED 33 T1¾ Translucent, 8mA LED
Resistor 40 1.0M ohm
Resistor 42 200 k ohm
Resistor 44 50 k ohm
Resistor 46 20 k ohm
Resistor 56 10 k ohm
Resistor 58 10 k ohm
Comparator 60 Type LM358
Diodes 62–68 Type 1N4148
Capacitor 80 0.1 μF
Resistor 82 100 ohm Diodes 84, 86 Type 1N4148

In operation, one of the switches 48, 50, 52, 54 is closed by a user to select one of the reference resistors 40, 42, 44, 46. By selecting a reference resistor with a high resistance, the reference purity level with which the measured contaminant level is compared is set higher. In contrast, selecting a reference resistor with a low resistance lowers the reference purity level. As an example, the reference resistor 40, which preferably has resistance of 1M ohm, is assumed to be selected by closing the switch 48 and leaving the other switches 50, 52, 54 open. As result, a voltage divider circuit is formed by the reference resistor 40 and the resistance of the water across the probes 16, 17.

When the circuitry 28 is supplied with 6 VAC across the power input terminals 36, 38 by the power transformer unit 30, the voltage formed between the switch 40 and the probe 16, the measured voltage, is supplied to the input terminal 72, and the voltage formed between the two resistors 56, 58, the reference voltage, is supplied to the input terminal 70. As noted above, the diodes 62, 64, 66, 68 rectify the 6 VAC into 6 VDC, which is supplied across terminals 69 and 71 of the comparator 60 to make the comparator operational.

When the resistance of the water across the test probes 16, 17 is greater than the reference resistance of 1M ohm, i.e., when the purity level of the water exceeds the reference purity level, the measured voltage applied to the input terminal 72 of the comparator 60 will be greater than the reference voltage applied to the input terminal 70, during the half cycle when the 6 VAC is being applied to the power terminal 36. As a result, the output at the terminal 74 of the comparator 60 will be low during this half cycle. This allows current to flow through the green LED 32 in the direction indicated by an arrow 76 and causing it to light, which indicates to the user that the purity level of the water exceeds the reference purity level.

It should be noted, however, that during the other half of the cycle, i.e., when the 6 VAC is being applied to the terminal 38, the measured voltage applied to the input terminal 72 is less than the reference voltage at the input terminal 70. As a result, the output at the terminal 74 is high, and accordingly, no current flows though the green LED 32 and the diode is not lit. However, the LED 32 will appear to be continually lit to the user.

When the resistance of the water across the probes 16, 17 is less than the reference resistance of 1M ohm, i.e., when the purity level of the water falls below the reference purity level, the measured voltage applied to the input terminal 72 of the comparator 60 will be greater than the reference voltage applied to the input terminal 70, during the half cycle when the 6 VAC is being applied to the input power terminal 38. As a result, the output at the terminal 74 of the comparator 60 will be low during this half cycle. This allows current to flow through the red LED 33 in the direction indicated by an arrow 78 and causing it to light, which indicates to the user that the purity level of the water is below the reference purity level.

Similar to the case when the resistance of the water is greater than the reference resistance, the red LED 33 is not lit during the other half of the cycle, i.e., when the 6 VAC is being applied to the power input terminal 36. This condition also is not noticeable to the user, since the red LED 33 will appear as if it is lit continually.

It will be appreciated that a significant advantage of the present invention is that contaminants in water are prevented from accumulating on the test probes of a purity indicator by applying AC voltage to the probes. Another advantage is that the present invention does not require any additional dedicated circuitry for preventing contaminant accumulation, and thereby simplifying circuit assembly process and reducing manufacturing cost. Also, the accuracy of water purity level detection is not affected by the accuracy of the 6 VAC input power.

While particular embodiments of the water quality indicator of the invention have been shown and described, it will be appreciated by those skilled in the art that changes and modifications may be made thereto without departing from the invention in its broader aspects and as set forth in the following claims.

What is claimed is:

1. Water purity indicating apparatus adapted to operate on AC input power, comprising:

a housing;

a pair of test probes extending from said housing for measuring a resistance of water; and circuit means connected to said test probes and provided within said housing for outputting a signal indicating a purity level of water based on a first AC voltage generated by said measured resistance of water.

2. The apparatus as defined in claim 1 wherein said circuit means includes:

at least one reference resistor representing a reference purity level and being operatively connectable to said test probes for producing said first AC voltage in conjunction with said measured resistance of water;

reference voltage generating means for generating a second AC voltage; and comparator means for comparing said first voltage with said second voltage, and generating said signal indicating said purity level of water relative to said reference purity level.

3. The apparatus as defined in claim 2, wherein said circuit means further includes a full-wave rectifier for rectifying the AC input power into DC operating power and supplying said DC operating power to said comparator means.

4. The apparatus as defined in claim 2 further including at least one displaying means operatively connected to said comparator means for displaying said purity level of water based on said signal indicating said purity levels of water output by said comparator means.

5. The apparatus as defined in claim 4, wherein at least one indicating means includes a first indicating means which is activated when said purity level of water is greater than said reference purity level and a second indicating means which is activated when said purity level of water is below said reference purity level.

6. The apparatus as defined in claim 5, wherein said first and said second indicating means are light emitting diodes having different colors.

7. The apparatus as defined in claim 1 further including power supply means for supplying the AC input power to said circuit means.

8. The apparatus as defined in claim 7 wherein said power supply means is a power transformer.

9. The apparatus as defined in claim 1, wherein said reference voltage generating means is a pair of resistors connected in series between a pair of AC input voltage terminals.

10. The apparatus as defined in claim 9, wherein said first AC voltage is developed between said pair of resistors.

11. AC power operated apparatus for measuring a resistance of water, comprising:

at least one reference resistor for providing a reference resistance;

a pair of test probes operatively connectable to said reference resistor for measuring the resistance of water;

reference voltage generating means for generating a first AC voltage; and comparator means for comparing said first AC voltage with a second AC voltage produced by said reference resistance and the water resistance, and generating a signal indicating the resistance of water relative to said reference resistance.

12. The apparatus as defined in claim 11, wherein said at least one reference resistor and said test probes are connected in series between a pair of AC input voltage terminals.

13. The apparatus as defined in claim 11, wherein said comparator means is a comparator.

14. The apparatus as defined in claim 11, further including reference resistance selecting means operatively connectable to said at least one reference resistor for selecting said reference resistance.

15. The apparatus as defined in claim 11, further including at least one displaying means operatively connected to said comparator means for displaying said signal indicating the resistance of water relative to said reference resistance.

16. The apparatus as defined in claim 15, wherein at least one indicating means includes a first indicating means which is activated when the resistance of water is less than said reference resistance, and a second indicating means which is activated when said resistance of water is greater than said reference resistance.

17. The apparatus as defined in claim 16, wherein said first and second indicating means are differently colored light emitting diodes.

18. The apparatus as defined in claim 11, further including a full-wave rectifier for rectifying AC voltage into DC operating voltage and supplying said DC operating voltage to said comparator means.

* * * * *